US009278058B2

(12) United States Patent
Nakamura et al.

(10) Patent No.: US 9,278,058 B2
(45) Date of Patent: Mar. 8, 2016

(54) MELANIN PRODUCTION INHIBITOR

(71) Applicant: Shiseido Company, Ltd., Chuo-ku, Tokyo (JP)

(72) Inventors: Mio Nakamura, Yokohama (JP); Shinichiro Haze, Yokohama (JP); Akira Ito, Yokohama (JP); Rumiko Fujiwara, Yokohama (JP); Takako Shibata, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 14/442,850

(22) PCT Filed: Nov. 14, 2013

(86) PCT No.: PCT/JP2013/080832

§ 371 (c)(1),
(2) Date: May 14, 2015

(87) PCT Pub. No.: WO2014/077334

PCT Pub. Date: May 22, 2014

(65) Prior Publication Data

US 2015/0290097 A1 Oct. 15, 2015

(30) Foreign Application Priority Data

Nov. 15, 2012 (JP) ................................ 2012-251422

(51) Int. Cl.
*A61K 8/37* (2006.01)
*A61Q 19/02* (2006.01)

(52) U.S. Cl.
CPC . *A61K 8/37* (2013.01); *A61Q 19/02* (2013.01); *A61K 2800/782* (2013.01)

(58) Field of Classification Search
CPC .... A61K 8/37; A61K 2800/782; A61Q 19/02
See application file for complete search history.

(56) References Cited

U.S. PATENT DOCUMENTS

2004/0248762 A1 12/2004 McGee et al.
2010/0239508 A1* 9/2010 Mori ....................... A61K 8/37 424/59

FOREIGN PATENT DOCUMENTS

JP 09-132527 A 5/1997
JP 10-273417 A 10/1998
JP 2006-160701 A1 6/2006
JP 2009-256215 A 11/2009

* cited by examiner

*Primary Examiner* — Shailendra Kumar
(74) *Attorney, Agent, or Firm* — Foley & Lardner LLP

(57) ABSTRACT

Provided is a novel drug capable of inhibiting excessive formation of melanin in skin and a skin whitening agent incorporated therewith.
Phenylethyl cinnamate is incorporated as an active ingredient.

2 Claims, No Drawings

MELANIN PRODUCTION INHIBITOR

TECHNICAL FIELD

The present invention relates to a melanin formation inhibitor or skin whitening agent obtained by containing phenylethyl cinnamate as an active ingredient thereof.

BACKGROUND ART

Melanin is a blackish-brown pigment produced by melanocytes present in epidermis, and is an insoluble high molecular weight compound formed by an oxidative condensation reaction by the action of enzymes such as tyrosinase using the amino acid, tyrosine, as a substrate. More specifically, melanin is classified into eumelanin, which exhibits black color, and pheomelanin, which exhibits red color. After being produced by melanocytes, these melanins are transferred in the form of melanin-containing granules (melanosomes) to epidermal keratinocytes present in the periphery thereof, and are excreted from epidermis accompanying turnover thereof. However, as a result of excessive production of melanin by melanocytes that have been activated by such factors as exposure to ultraviolet rays or stress and the subsequent deposition thereof, pigmentation, age spots, freckles or liver spots and the like appear on the skin following sun tanning, thereby becoming a source of concern in terms of aesthetics.

In the past, in addition to cysteine, glutathione and vitamin C, products derived from microorganisms belonging to the genus *Trichoderma* (Patent Document 1), lactoferrin hydrolysates (Patent Document 2), and amino acid derivatives and peptide derivatives of kojic acid (Patent Document 3) have been reported to have tyrosinase inhibitory action and be able to inhibit the formation of melanin, while specific aromatic compounds such as furanone have been reported to be able to be used as tyrosinase inhibitors and melanin formation inhibitors (Patent Documents 4, 5 and 6).

Moreover, the known α-irone, 4-(2,5,6,6-tetramethyl-cyclohexen-1-yl)-3-buten-2-one (Patent Document 7), γ-irone and precursors of α-irone in the form of iriflorental and iribaridal (Patent Document 8) have been reported to have melanin inhibitory effects.

However, there are cases in which conventionally known melanin formation inhibitors have problems with safety in the manner of hydroquinone, which has recently attracted attention as a skin whitening agent, or the effects thereof may not be adequate in terms of practical use, thereby resulting in a continuing need to search for a novel component having melanin formation inhibitory action.

PRIOR ART DOCUMENTS

Patent Documents

Patent Document 1: Japanese Unexamined Patent Publication No. H2-145189

Patent Document 2: Japanese Unexamined Patent Publication No. H5-320068

Patent Document 3: Japanese Unexamined Patent Publication No. H4-187618

Patent Document 4: Japanese Unexamined Patent Publication No. 2000-302642

Patent Document 5: Japanese Unexamined Patent Publication No. 2001-163719

Patent Document 6: Japanese Unexamined Patent Publication No. 2001-240528

Patent Document 7: Japanese Unexamined Patent Publication No. 2011-157286

Patent Document 8: Japanese Unexamined Patent Publication No. H9-241154

DISCLOSURE OF THE INVENTION

Problems to be Solved by the Invention

An object of the present invention is to provide a novel melanin formation inhibitor having superior safety and significant action.

Means for Solving the Problems

As a result of conducting extensive studies towards solving the aforementioned problems, the inventor of the present invention found that phenylethyl cinnamate has superior melanin inhibitory effects without demonstrating cytotoxicity.

Thus, the present application includes the inventions indicated below.

[1] A melanin formation inhibitor containing phenylethyl cinnamate as an active ingredient thereof.

[2] A skin whitening agent containing phenylethyl cinnamate as an active ingredient thereof.

[3] An aesthetic or therapeutic method for inhibiting excessive melanin formation in skin, comprising: applying phenylethyl cinnamate to a subject requiring inhibition of excessive melanin formation in skin.

[4] A skin whitening method, comprising: applying phenylethyl cinnamate to a subject requiring skin whitening.

[5] A use of phenylethyl cinnamate for inhibiting excessive melanin formation in skin.

[6] A use of phenylethyl cinnamate for whitening skin.

Effects of the Invention

According to the present invention, excessive melanin formation in skin can be significantly inhibited. Consequently, the melanin formation inhibitor of the present invention can be used as a skin whitening agent that is effective for preventing and/or improving pigmentation, age spots, freckles or liver spots and the like following sun tanning. In addition, since the synthetic aromatic contained as a component of the melanin formation inhibitor of the present invention is nature identical (NI) in that the presence thereof is frequently observed in nature and demonstrates hardly any cytotoxicity, it has adequate safety for use in cosmetics or pharmaceuticals.

MODE FOR CARRYING OUT THE INVENTION

As will be described in detail in the subsequent examples, screening for aromatic components of the melanin formation inhibitor was carried out by allowing various candidate aromatics to act on B16 melanoma, and evaluating cytotoxicity and the ratio of the amount of melanin (%) in comparison with a control (addition of solvent only).

As a result thereof, phenylethyl cinnamate was found to have superior melanin formation inhibitory effects without demonstrating cytotoxicity.

Phenylethyl cinnamate (CAS name: 2-Phenylethyl 3-phenyl propenoate, CAS No.: 103-53-7)

Phenylethyl cinnamate is a compound having the chemical structure indicated below.

[Chemical Formula 1]

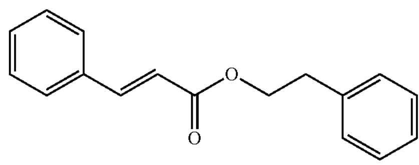

It is known as a compound having a balsamic fragrance that is present in trace amounts in nature, and is also frequently used as a flavoring.

The dosage, administration form and drug form of the melanin formation inhibitor or skin whitening agent of the present invention (to also be referred to as the "present agent") can be suitably determined according the purpose of use thereof. For example, the aromatic compound contained in the present agent as an active ingredient is typically incorporated at 0.00001% by weight to 10% by weight, preferably at 0.0001% by weight to 1% by weight, and optimally at 0.0001% by weight to 0.1% by weight based on the total weight of the drug. Although there are no particular limitations on the administration form of the present agent, and it may be administered orally, parenterally, externally or by inhaling and the like, it is preferably a skin external agent. Examples of drug forms include external preparations such as ointments, creams, milky lotions, lotions, packs or bath additives, parenteral preparations such as injections, intravenous infusions or suppositories, and oral preparations such as tablets, powders, capsules, granules, extracts or syrups. In particular, cosmetics such as perfumes, colognes, shampoos, rinses, skin care products, body shampoos, body rinses, body powders, air fresheners, deodorants, bath additives, lotions, creams, soaps, toothpastes or aerosol products, and other forms commonly used in aromatics, are preferable.

In addition, the present agent can also suitably incorporate as necessary other components in addition to the aforementioned essential components such as components normally used in foods or pharmaceuticals in the manner of excipients, desiccants, fortifiers, thickeners, emulsifiers, antioxidants, sweeteners, sour agents, flavorings, colorants or aromatics, as well as components normally used in cosmetics in the manner of skin whitening agents, moisturizers, oily components, ultraviolet absorbers, surfactants, thickeners, alcohols, powdered components, coloring agents, aqueous components, water or various types of skin nutrients.

Moreover, in the case of using the present agent as an external skin agent, assistants commonly used in external skin agents can be suitably incorporated therein, examples of which include sequestering agents such as disodium edetate, trisodium edetate, sodium citrate, sodium polyphosphate, sodium metaphosphate or gluconic acid, hot water extracts such as caffeine, tannin, verapamil, tranexamic acid and derivatives thereof, glabridin or quince fruit, various types of natural herbs, drugs such as tocopherol acetate, glycyrrhizic acid and derivatives thereof, and salts thereof, skin whitening agents such as vitamin C, magnesium ascorbyl phosphate, ascorbic acid glucoside, albumin or kojic acid, sugars such as glucose, fructose, mannose, sucrose or trehalose, and vitamin A such as retinoic acid, retinol, retinol acetate or retinol palmitate.

The following provides a more detailed explanation of the present invention by indicating examples thereof. Furthermore, the present invention is not limited thereto.

EXAMPLES

1) Cell Seeding and Addition of Test Substance

Mouse B16 melanoma cells were disseminated in a 6-well plate at 100,000 cells/well. On the following day, a test substance solution (solvent: ethyl alcohol) was added and used in a cell proliferation test and melanin formation inhibition test. A nature identical synthetic aromatic in the form of phenylethyl cinnamate (Toyotama International Inc.) was used for the test substance, and it was used in the tests indicated below.

2) Cell Proliferation Test

After aspirating off the medium 3 days after adding the test substance solution, 1 ml of EMEM medium containing 10% alamar blue solution was added and allowed to react at 37° C. 30 minutes later, 100 μl were transferred to a 94-well plate followed by measurement of fluorescence at an excitation wavelength of 544 nm and measurement wavelength of 590 nm. The ratio of the number of cells (% number of cells) of a test substance addition group based on a value of 100 for a test substance non-addition group (addition of solvent only) was calculated by using that value as a relative value of the number of viable cells. A higher value for % number of cells means a lower level of cytotoxicity.

3) Melanin Formation Inhibition Test

The medium was aspirated off 3 days after addition of test substance, and after washing using a buffer (50 mM phosphate buffer, pH 6.8), 1 M NaOH solution was added to lyse the cells followed by measurement of absorbance at 475 nm. The ratio of the amount of melanin (%) of a test substance addition group based on a value of 100 for a test substance non-addition group (addition of solvent only) was calculated using that value as a relative value of the amount of melanin. A lower value for the ratio of the amount of melanin means higher melanin formation inhibitory effects.

The results of the aforementioned cell proliferation test and melanin formation inhibition test are indicated below.

TABLE 1

| Test Compound | Test Substance Final Concentration (ppm) | Ratio of Amount of Melanin (%) | No. of Cells (%) |
|---|---|---|---|
| Phenylethyl | 1 | 82 | 94 |
| Cinnamate | 2 | 74 | 92 |

As is clear from the above results, phenylethyl cinnamate demonstrated superior melanin formation inhibitory effects while demonstrating hardly any cytotoxicity.

Although the following indicates formulation examples of the present agent, carrying out the present invention is not limited to the following examples.

Milky Lotion

| Formula | (wt %) |
|---|---|
| (1) Stearic acid | 2.0 |
| (2) Cetyl alcohol | 1.5 |
| (3) Vaseline | 4.0 |
| (4) Squalane | 5.0 |
| (5) Glycerol tri-2-ethylhexanoate | 2.0 |
| (6) Sorbitan monooleate | 2.0 |
| (7) Dipropylene glycol | 5.0 |
| (8) PEG1500 | 0.3 |
| (9) Triethanolamine | 0.1 |
| (10) Preservative | As suitable |
| (11) Melanin formation inhibitor of present invention: Phenylethyl cinnamate | 0.0005 |
| (12) Purified water | Balance |

Cream

| Formula | (wt %) |
|---|---|
| (1) Glycerin | 10.0 |
| (2) Butylene glycol | 5.0 |
| (3) Carbomer | 0.1 |
| (4) Potassium hydroxide | 0.2 |
| (5) Stearic acid | 2.0 |
| (6) Glyceryl stearate | 2.0 |
| (7) Glyceryl isostearate | 2.0 |
| (8) Vaseline | 5.0 |
| (9) Preservative | As suitable |
| (10) Antioxidant | As suitable |
| (11) Melanin formation inhibitor of present invention: Phenylethyl cinnamate | 0.002 |
| (12) Purified water | Balance |
| (13) Chelating agent | As suitable |
| (14) Pigment | As suitable |
| (15) Stearyl alcohol | 2.0 |
| (16) Behenyl alcohol | 2.0 |
| (17) Hydrogenated palm oil | 2.0 |
| (18) Squalane | 10.0 |
| (19) Potassium 4-methoxysalicylate | 3.0 |

Cream

| Formula | (wt %) |
|---|---|
| (1) Glycerin | 3.0 |
| (2) Dipropylene glycol | 7.0 |
| (3) Polyethylene glycol | 3.0 |
| (4) Glyceryl stearate | 3.0 |
| (5) Glyceryl isostearate | 2.0 |
| (6) Stearyl alcohol | 2.0 |
| (7) Behenyl alcohol | 2.0 |
| (8) Liquid paraffin | 7.0 |
| (9) Cyclomethicone | 3.0 |
| (10) Dimethicone | 1.0 |
| (11) Octyl methoxycinnamate | 0.1 |
| (12) Sodium hyaluronate | 0.05 |
| (13) Preservative | As suitable |
| (14) Antioxidant | As suitable |
| (15) Damascenone | 0.001 |
| (16) Melanin formation inhibitor of present invention: Phenylethyl cinnamate | 0.0005 |
| (17) Purified water | Balance |
| (18) Chelating agent | As suitable |
| (19) Pigment | As suitable |

Gel

| Formula | (wt %) |
|---|---|
| (1) Ethyl alcohol | 10.0 |
| (2) Glycerin | 5.0 |
| (3) Butylene glycol | 5.0 |
| (4) Carbomer | 0.5 |
| (5) Aminomethyl propanol | 0.3 |
| (6) PEG-60 hydrogenated castor oil | 0.3 |
| (7) Menthol | 0.02 |
| (8) Preservative | As suitable |
| (9) Chelating agent | As suitable |
| (10) Damascenone | 0.0004 |
| (11) Melanin formation inhibitor of present invention: Phenylethyl cinnamate | 0.0005 |
| (12) Purified water | Balance |

Aerosol

| Formula | (wt %) |
|---|---|
| (1) Glycerin | 2.0 |
| (2) Dipropylene glycol | 2.0 |
| (3) PEG-60 hydrogenated castor oil | 2.0 |
| (4) HPβCD | 1.0 |
| (5) Preservative | As suitable |
| (6) Chelating agent | As suitable |
| (7) Dye | As suitable |
| (8) Melanin formation inhibitor of present invention: Phenylethyl cinnamate | 0.001 |
| (9) Purified water | As suitable |
| (10) LPG | Balance |

Fragrance

| Formula | (wt %) |
|---|---|
| (1) Alcohol | 75.0 |
| (2) Purified water | Balance |
| (3) Dipropylene glycol | 5.0 |
| (4) Damascenone | 0.0005 |
| (5) Melanin formationinhibitor of present invention: Phenylethyl cinnamate | 0.002 |
| (6) Preservative | 8.0 |
| (7) Pigment | As suitable |
| (8) Ultraviolet absorber | As suitable |

The invention claimed is:

1. An aesthetic or therapeutic method for inhibiting excessive melanin formation in skin, comprising: applying phenylethyl cinnamate to a subject in need of inhibition of excessive melanin formation in skin.

2. A skin whitening method, comprising: applying phenylethyl cinnamate to a subject in need of skin whitening.

* * * * *